US00PP09549P

United States Patent [19]

Zaiger et al.

[11] Patent Number: Plant 9,549

[45] Date of Patent: May 14, 1996

[54] PEACH TREE "VISTA"

[76] Inventors: Chris F. Zaiger, 929 Grimes Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 434,647

[22] Filed: Apr. 20, 1995

[51] Int. Cl.[6] ..... A01H 5/00

[52] U.S. Cl. ..... Plt./43.1

[58] Field of Search ..... Plt./43.1

*Primary Examiner*—James R. Feyrer

[57] ABSTRACT

Our new development is a new and distinct variety of peach tree whose novelty consists of the following unique combination of desirable features:

1. Heavy and regular production of large size fruit.
2. Fruit with firm flesh, good storage and shipping ability.
3. The ability of the fruit to hold firm on the tree 6–7 days after maturity (shipping ripe).
4. Fruit with a high degree of attractive red skin color.
5. Fruit with good flavor and eating quality.
6. Vigorous and upright growth.
7. Relatively uniform ripening of the fruit throughout the tree.

1 Drawing Sheet

ORIGIN OF THE VARIETY

The new variety of peach tree was developed by us in our experimental orchard located near Modesto, Calif., as an open pollinated seedling of Rich Lady Peach (U.S. Plant Pat. No. 7,290). A large number of these open pollinated seedlings were grown under careful observation and the above seedling having been especially desirable with respect to its fruit was selected for asexual reproduction and commercialization.

ASEXUAL REPRODUCTION OF THE VARIETY

The present new variety of peach tree was asexually reproducd by budding, as performed by us in our experimental orchard ocated near Modesto, Calif., which shows that said characteristics come true to the original tree and are established and transmitted through succeeding propagations.

SUMMARY OF THE VARIETY

The present new variety of peach tree is of large size, vigorous, upright growth and is a regular and productive bearer of large size, firm, yellow flesh, semi clingstone fruit with good flavor and eating quality. The fruit is further characterized by being relatively uniform is size throughout the tree, holding firm on the tree 6 to 7 days after maturity (shipping ripe), having good storage and shipping quality and an attractive red skin color; in comparison to its seed parent Rich Lady Peach (U.S. Plant Pat. No. 7,290) the new variety is approximately 6 to 7 days later in maturity.

DESCRIPTION OF THE PHOTOGRAPHS

The accompanying photographic illustration shows typical specimens of the foliage and fruit of the present new variety of peach tree. The upper and lower surface of the leaves are shown as well as a fruit divided in its suture plane to reveal flesh coloration, pit cavity and a stone remaining in place. The photographic illustration was taken shortly after the fruit was picked at maturity (shipping ripe) and the colors are as nearly true as reasonably possible in a color representation of this type.

DESCRIPTION OF THE VARIETY

The botanical detailed description of the present new and distinct variety of peach tree, its flowers, foliage and fruit are based on observations of specimens grown near Modesto, Calif., with color terminaolgy (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Productivity.*—Productive.
- *Bearer.*—Regular.

Trunk:
- *Size.*—Large.
- *Texture.*—Medium shaggy.
- *Color.*—Brown to grayish brown (5-E-7) to (5-E-8).

Branches:
- *Size.*—Medium to large.
- *Texture.*—Smooth to medium rough. Varies with age of growth.
- *Lenticls.*—Medium to large. Numerous.
- *Color.*—Light brown to brown (5-D-5) to (5-D-6).

Leaves:
- *Size.*—Large. Average length 6¼". Average width 1½".
- *Texture.*—Smooth.
- *Petiole.*—Size: Medium. Average length ½". Medium thickness.
- *Form.*— Lanceolate. Pointed.
- *Thickness.*—Medium.
- *Glands.*—Reniform. Medium to large. Number varies from 1 to 4. Average number 2. Positioned on base of leaf blade and upper position of Petiole.
- *Margin.*—Crenate.
- *Color.*—Upper surface — green to dark green (29-F-5) to (29-F-7). Lower surface — dull green to green (29-E-6) to (29-E-8).

Flower buds:
- *Size.*—Large.
- *Form.*—Plump.
- *Pubescence.*—Pubescent.

Flower:
- *Size.*—Large — showy.
- *Blooming period.*—Mar. 1, 1993 to Mar. 9, 1993. Varies slightly with climatic conditions.

*Pollen.*—Present.
*Color.*—Pink.

Fruit:
*Maturity when described.*—Firm ripe.
*Date of first picking.*—Jun. 13, 1993.
*Date of last picking.*—Jun. 21, 1993. Varies slightly with climatic conditions.
*Size.*—Large. Comparatively uniform. Average diameter axially 3". Average transversely in suture plane 3".
*Form.*—Globose — slightly flattened at stem end.
*Suture.*—Shallow — extends from base to apex.
*Ventral surface.*— Varies from rounded to slightly lipped.
*Cavity.*—Rounded to slightly elongated in suture plane. Average depth ½". Average breadth ¾".
*Apex.*—Varies from slight pistil point to slight depression.

Flesh:
*Texture.*—Firm.
*Ripens.*—Evenly.
*Fibers.*—New — tender.
*Juice.*—Moderate.
*Flavor.*—Good — mild, with a good balance between surgar and acid.
*Eating quality*—Good.
*Aroma.*—Slight to moderate.
*Amygdalin.*—Undetected.
*Color.*—Yellow to butter yellow (4-A-5) to (4-A-7). Pit cavity — light red to signal red (10-A-7) to (10-A-8) — flesh torn form stone dull yellow to grayish yellow (3-B-3) to (3-C-4).

Skin:
*Thickness.*—Medium.
*Texture.*—Medium.
*Tendency to crack.*—None.
*Down.*—Moderate. Medium length.
*Color.*—Yellow ground color (4-A-5) to (4-A-7). Overspread with red blush (10-B-8) to (10-D-8).

Stone:
*Type.*—Semi-clingstone. Nearly free when soft ripe.
*Size.*—Large. Average length 1⅜". Average breadth 1⅛". Average thickness ¾".
*Form.*—Ovoid.
*Base.*—Mostly rounded — varies from sraight to rounded.
*Apex.*—Acuminate.
*Sides.*—Mostly equal, varies from equal to unequal.
*Surface.*—Irregular furrowed toward apex with longest furrows near outer edges. Pitted toward base, pit cavities vary from round to elongated.
*Tendency to split.*—Very slight.
*Color.*—Brownish red to reddish brown (8-C-6) to (8-D-8).

Use: Dessert.
*Market.*—Local and long distance.

Keeping quality: Good.

Shipping quality: Good.

The present new and distinct variety of peach tree, its flowers, foliage and fruit herein described may vary in slight detail due to the cultural practices, soil types and climatic conditions under which the variety may be grown. The present description is of the variety grown under the ecological conditions prevailing near Modesto, Calif.

We claim:

1. A new and distinct variety of peach tree, substantially as illustrated and described, characterized by its large size, vigorous, upright growth, which is a productive and regular bearer of large, yellow flesh, semi clingstone fruit with good flavor and eating quality; the fruit is further characterized by having firm flesh with good storage and shipping quality, holding on the tree 6 to 7 days after maturity (shipping ripe), having an attractive red skin color and in comparison to its seed parent Rich Lady Peach (U.S. Plant Pat. No. 7,290) the new variety is approximately 6 to 7 days later in maturity.

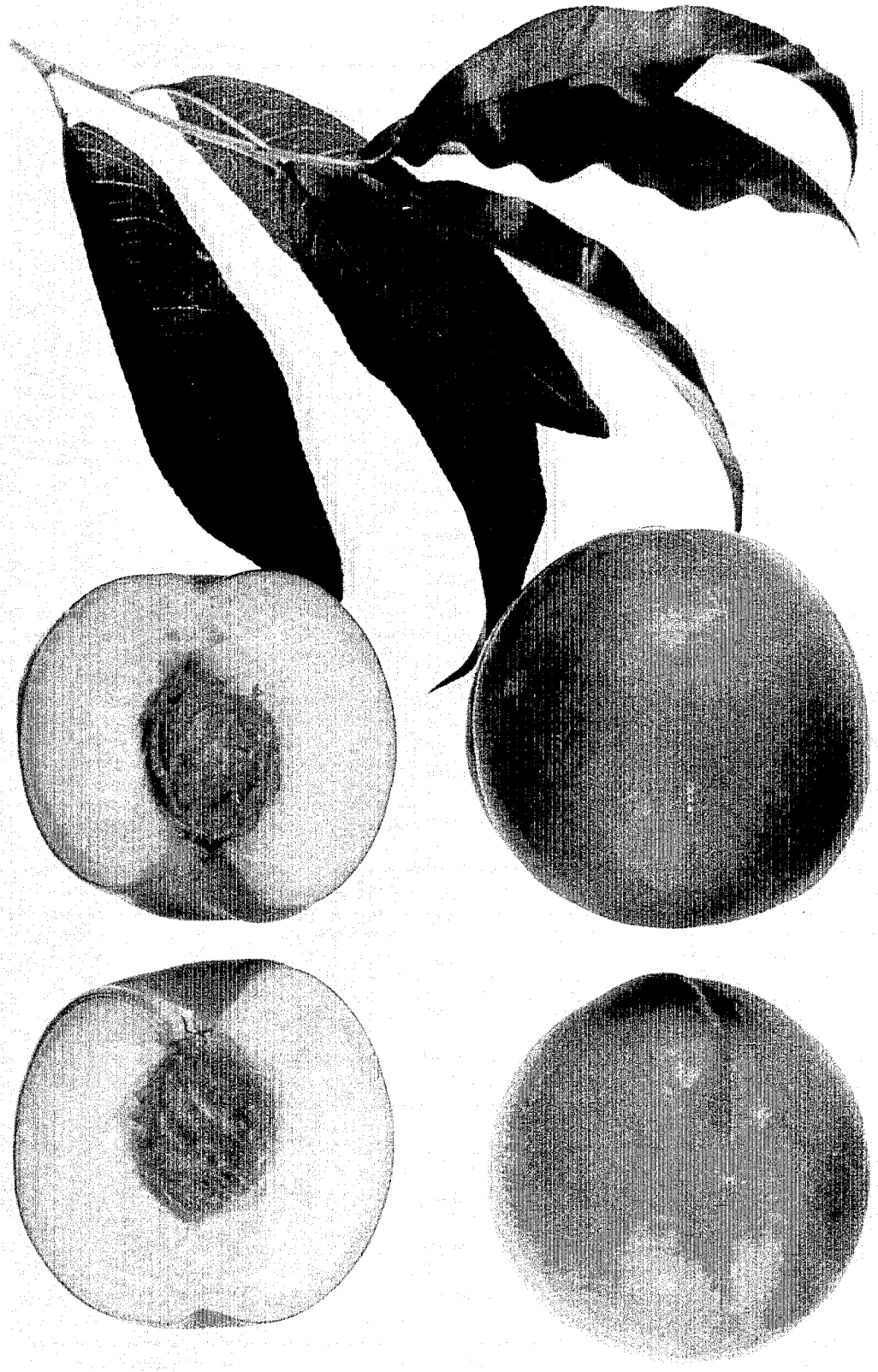

* * * * *